US012805951B2

(12) United States Patent
Ninni et al.

(10) Patent No.: US 12,805,951 B2
(45) Date of Patent: Nov. 24, 2026

(54) DISTRIBUTED BENDING FOR BENDABLE MEDICAL DEVICES

(71) Applicant: CANON U.S.A., INC., Melville, NY (US)

(72) Inventors: Brian Ninni, Woburn, MA (US); Takahisa Kato, Brookline, MA (US)

(73) Assignee: CANON U.S.A., INC., Melville, NY (US)

( * ) Notice: Subject to any disclaimer, the term of this patent is extended or adjusted under 35 U.S.C. 154(b) by 150 days.

(21) Appl. No.: 18/816,580

(22) Filed: Aug. 27, 2024

(65) Prior Publication Data

US 2025/0072981 A1 Mar. 6, 2025

Related U.S. Application Data

(60) Provisional application No. 63/579,727, filed on Aug. 30, 2023.

(51) Int. Cl.
*A61B 34/30* (2016.01)
*A61B 1/005* (2006.01)

(52) U.S. Cl.
CPC ............ *A61B 34/30* (2016.02); *A61B 1/0053* (2013.01)

(58) Field of Classification Search
None
See application file for complete search history.

(56) References Cited

U.S. PATENT DOCUMENTS

| | | | |
|---|---|---|---|
| 6,201,387 | B1 | 3/2001 | Govari |
| 9,144,370 | B2 | 9/2015 | Kato et al. |
| 10,687,694 | B2 | 6/2020 | Tanaka et al. |
| 11,007,641 | B2 | 5/2021 | Takagi et al. |
| 11,051,892 | B2 | 7/2021 | Hata et al. |
| 11,096,552 | B2 | 8/2021 | Hata et al. |
| 11,103,992 | B2 | 8/2021 | Tanaka et al. |
| 11,278,366 | B2 | 3/2022 | Kose et al. |
| 11,504,501 | B2 | 11/2022 | Kato et al. |
| 11,559,190 | B2 | 1/2023 | Okumura et al. |
| 11,571,268 | B1 | 2/2023 | Masaki et al. |
| 11,622,828 | B2 | 4/2023 | Kincaid et al. |
| 2007/0135803 | A1 | 6/2007 | Belson |
| 2012/0271109 | A1 | 10/2012 | Belson |

(Continued)

FOREIGN PATENT DOCUMENTS

| | | | |
|---|---|---|---|
| JP | 2016-501622 | A | 1/2016 |
| JP | 2017-523020 | A | 8/2017 |

(Continued)

*Primary Examiner* — Michael W Kahelin
(74) *Attorney, Agent, or Firm* — Canon U.S.A., Inc. IP Division

(57) ABSTRACT

Provided herein is a robot apparatus, system and method of use. The robot system may comprise a bendable body having a plurality of steerable segments and a controller, where the controller controls actuation of the steerable segments based on an input data. In some embodiments, the input data is at least one of: a target bend, or a data representation of target bend. In some embodiments, the input data of operation mode may be the selection of a Distributed bending mode, wherein the controller is configured to move the at least one proximal drive wire and the at least one distal drive wire simultaneously.

17 Claims, 7 Drawing Sheets

(56) References Cited

U.S. PATENT DOCUMENTS

| | | | | |
|---|---|---|---|---|
| 2013/0096497 | A1* | 4/2013 | Duindam | A61B 34/30 604/95.01 |
| 2015/0088161 | A1 | 3/2015 | Hata et al. | |
| 2018/0192854 | A1* | 7/2018 | Hata | A61B 1/00006 |
| 2018/0243900 | A1 | 8/2018 | Tanaka et al. | |
| 2018/0296282 | A1 | 10/2018 | Kose et al. | |
| 2018/0311006 | A1 | 11/2018 | Kose et al. | |
| 2019/0015978 | A1 | 1/2019 | Takagi et al. | |
| 2019/0105468 | A1 | 4/2019 | Kato et al. | |
| 2020/0375665 | A1 | 12/2020 | Masaki et al. | |
| 2021/0121051 | A1 | 4/2021 | Altshuler et al. | |
| 2021/0121162 | A1 | 4/2021 | Ninni et al. | |
| 2021/0259521 | A1 | 8/2021 | Hwang | |
| 2021/0259790 | A1 | 8/2021 | Kaiser | |
| 2021/0259794 | A1 | 8/2021 | Kato et al. | |
| 2021/0260339 | A1 | 8/2021 | Ninni | |
| 2021/0260767 | A1 | 8/2021 | Masaki et al. | |
| 2021/0308423 | A1 | 10/2021 | Kincaid | |
| 2021/0362323 | A1 | 11/2021 | Tanaka et al. | |
| 2021/0369081 | A1 | 12/2021 | Kose | |
| 2021/0369085 | A1 | 12/2021 | Kato et al. | |
| 2021/0369355 | A1 | 12/2021 | Masaki et al. | |
| 2021/0369366 | A1 | 12/2021 | Hwang et al. | |
| 2021/0386972 | A1 | 12/2021 | Chang et al. | |
| 2022/0016394 | A1 | 1/2022 | Ninni | |
| 2022/0039635 | A1 | 2/2022 | Shia | |
| 2022/0039784 | A1 | 2/2022 | Hwang et al. | |
| 2022/0040450 | A1 | 2/2022 | Haubert | |
| 2022/0126060 | A1 | 4/2022 | Shia et al. | |
| 2022/0202273 | A1 | 6/2022 | Ninni | |
| 2022/0202277 | A1 | 6/2022 | Chang et al. | |
| 2022/0202500 | A1 | 6/2022 | Ninni et al. | |
| 2022/0202501 | A1 | 6/2022 | Zhang et al. | |
| 2022/0202502 | A1 | 6/2022 | Zhang et al. | |
| 2022/0203071 | A1 | 6/2022 | Hwang et al. | |
| 2023/0016761 | A1 | 1/2023 | Kaiser et al. | |
| 2023/0137954 | A1 | 5/2023 | Hwang et al. | |
| 2023/0201522 | A1 | 6/2023 | Hwang et al. | |
| 2023/0255442 | A1 | 8/2023 | Masaki et al. | |
| 2025/0143812 | A1* | 5/2025 | Masaki | A61B 34/10 |

FOREIGN PATENT DOCUMENTS

| | | | |
|---|---|---|---|
| JP | 2018-516128 | A | 6/2018 |
| WO | 2020/018934 | A1 | 1/2020 |
| WO | 2020/194212 | A1 | 10/2020 |
| WO | 2021/142272 | A1 | 7/2021 |
| WO | 2022/031995 | A1 | 2/2022 |
| WO | 2022/032162 | A1 | 2/2022 |
| WO | 2023/150162 | A1 | 8/2023 |
| WO | 2023/154246 | A1 | 8/2023 |
| WO | 2023/154352 | A1 | 8/2023 |
| WO | 2023/154713 | A1 | 8/2023 |
| WO | 2023/154825 | A1 | 8/2023 |
| WO | 2023/154931 | A1 | 8/2023 |

* cited by examiner

DISTRIBUTED BENDING FOR BENDABLE MEDICAL DEVICES

CROSS REFERENCE TO RELATED PATENT APPLICATIONS

This application claims priority from U.S. Provisional Patent Application No. 63/579,727 filed on Aug. 30, 2023, in the United States Patent and Trademark Office, the disclosure of which is incorporated by reference herein, in its entirety.

BACKGROUND

Field of the Disclosure

The present disclosure relates to medical devices. More particularly, the disclosure exemplifies embodiments of a steerable medical device, such as endoscopes or catheters that has multiple bendable sections.

Description of the Related Art

Endoscopy, bronchoscopy, catheterization, and other medical procedures facilitate the ability to look inside a body. During such a procedure, a flexible medical device may be inserted into a patient's body, and an instrument may be passed through the device to examine or treat an area inside the body. For viewing and/or treating the airway of a patient, a bronchoscope may be used. Medical tools such as cameras and biopsy needles may be inserted through a tool channel in the bronchoscope to target area in the patient for diagnosis, planning, medical procedure(s), treatment, etc.

Some of these medical devices are guided through a disposable or limited-use flexible tubular body often referred to as a sleeve or sheath or introducer sheath. Some of these introducer sheaths or sleeves are robotically controlled. A robotically controlled catheter or endoscope has a catheter sheath with a steerable distal section and a non-steerable proximal section. The proximal section connects to an actuator unit via an electromechanical connector, and the distal section is sized to be introduced into a patient's anatomy through natural orifices or small surgical incisions. Similar catheter or endoscopes insertable into a patient can be operated manually by a user without automated or robotic control. In either case, one or more channels extend along a central lumen of the sheath to allow access for imaging devices (miniature cameras or optical fiber probes) and/or end effectors (biopsy tools or therapy probes), and/or for passing fluids (contrast agents, gas, or flushing solutions).

Most catheters on the market today have a single steerable distal section, where the user has the ability to direct the bending motion of this steerable distal section. However, a new catheter with three steerable sections at the distal end of the catheter is in development. These steerable distal sections can be bent independently, and different operation modes are available. For example, the distal-most bending segment may be bent while the other sections are left unbend in the a Tip Bending mode of operation that is particularly useful for navigation of the steerable device in a lumen. In another mode, only the middle segment is bent (called Targeting mode, or Chickenhead mode since this movement looks like a chicken hunting for seeds on the ground—or more relevantly, a biopsy tool hunting for various biopsy locations. These modes are described in, for example, U.S. Pat. No. 11,096,552, herein incorporated by reference in its entirety.

However, additional modes optimizing the scope of movement allowed by a catheter having multiple distal bending sections (either the three exemplified in the above references or two, four, five, or more sections) have not been fully explored. Additionally, the transitions between the varying control modes has not been sufficiently addressed.

Thus, there is needed a flexible medical device with multiple distal steerable sections that has multiple control modes and a transition between these varying control modes that minimizes variabilities in the transition, is user friendly, and provides an optimal workflow and usability.

SUMMARY

Accordingly, it is a broad object of the present disclosure to provide a robot system, apparatus, and method of use. The robot system may comprise: a bendable body having a steerable distal section comprising: a distal bending segment that is bendable by at least one distal drive wire; a proximal bending segment that is bendable by at least one proximal drive wire; one or more first actuators configured to drive the distal drive wire; one or more second actuators configured to drive the proximal drive wire; and a controller for controlling the first and second actuators. The controller controls the actuators based on an input data of: an operation mode and at least one of: a target bend, or a data representation of target bend. In some embodiments, the input data of operation mode may be the selection of a Distributed bending mode, wherein the controller is configured to move the at least one proximal drive wire and the at least one distal drive wire simultaneously.

In some embodiments, the operation mode is selected from at least: (a) Tip Bending mode, (b) Targeting mode, and (c) Distributed bending mode.

The Tip Bending mode can be described wherein the controller is configured to move the at least one distal drive wire to bend the distal bending segment towards the target bend, or the data representation of target bend, based on input data. The Targeting mode may be described wherein the controller is configured to move the at least one proximal drive wire to bend the proximal bending segment towards the target bend or the data representation based on input data in the case of the bendable body having two bending segments, and wherein the controller is configured to move only an at least one drive wire to bend the bending segment proximal to the distal bending segment towards the target bend or the data representation of target bend based on input data in the case of the bendable body having three or more bending segments. The Distributed bending mode may be described, wherein the controller is configured to move the at least one proximal drive wire and the at least one distal drive wire simultaneously.

Further features of the present disclosure will become apparent from the following description of exemplary embodiments with reference to the attached drawings, where like structure is indicated with like reference numerals.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures.

Figure 1:
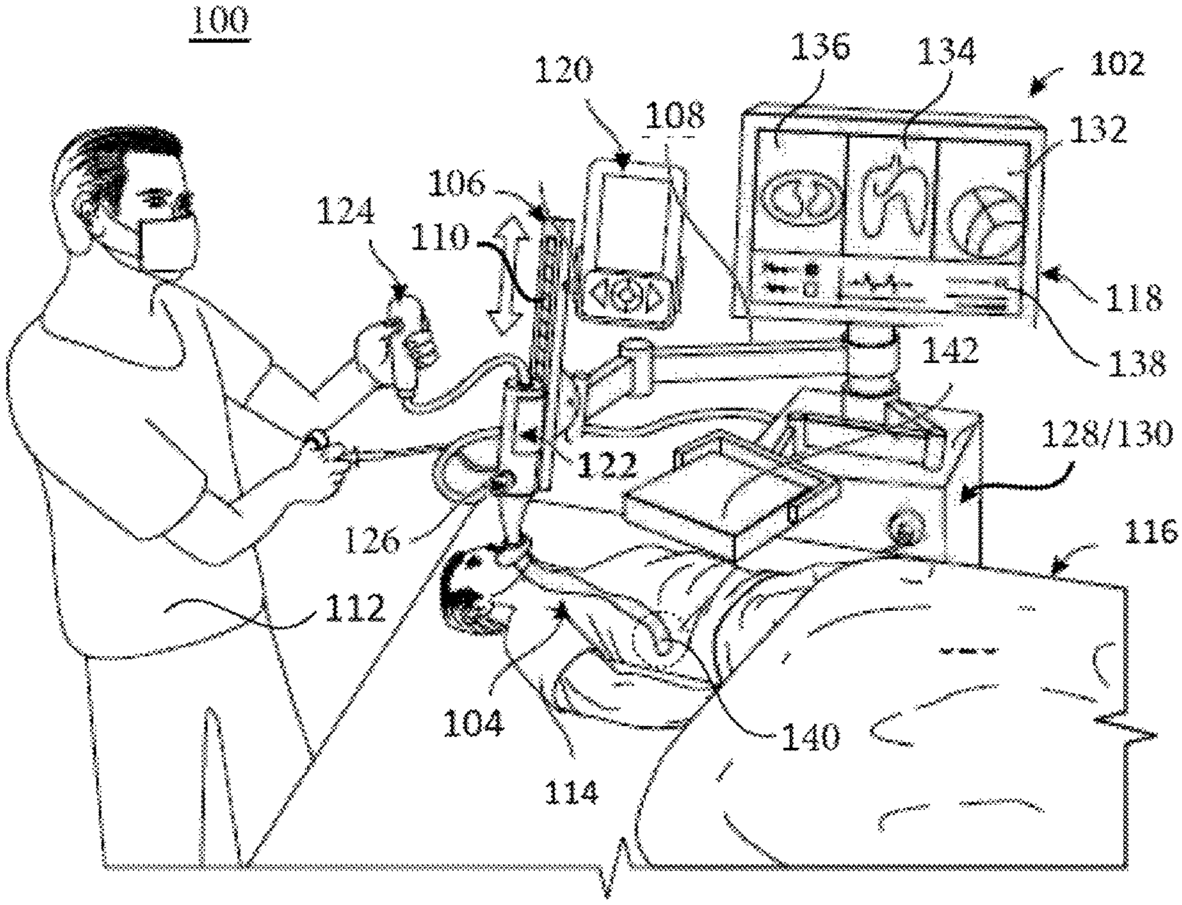
FIG. 1 illustrates at least one embodiment of an imaging, continuum robot, or endoscopic apparatus or system in accordance with one or more aspects of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DESCRIPTION OF THE EMBODIMENTS

The present disclosure has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The following paragraphs describe certain explanatory embodiments of a robotic medical system configured to use a bendable medical device, and particularly a bendable body. Other embodiments may include alternatives, equivalents, and modifications. Additionally, the explanatory embodiments may include several features, and a particular feature may not be essential to some embodiments of the devices, systems, and methods that are described herein.

<Robotic Catheter System>

Figure 2:
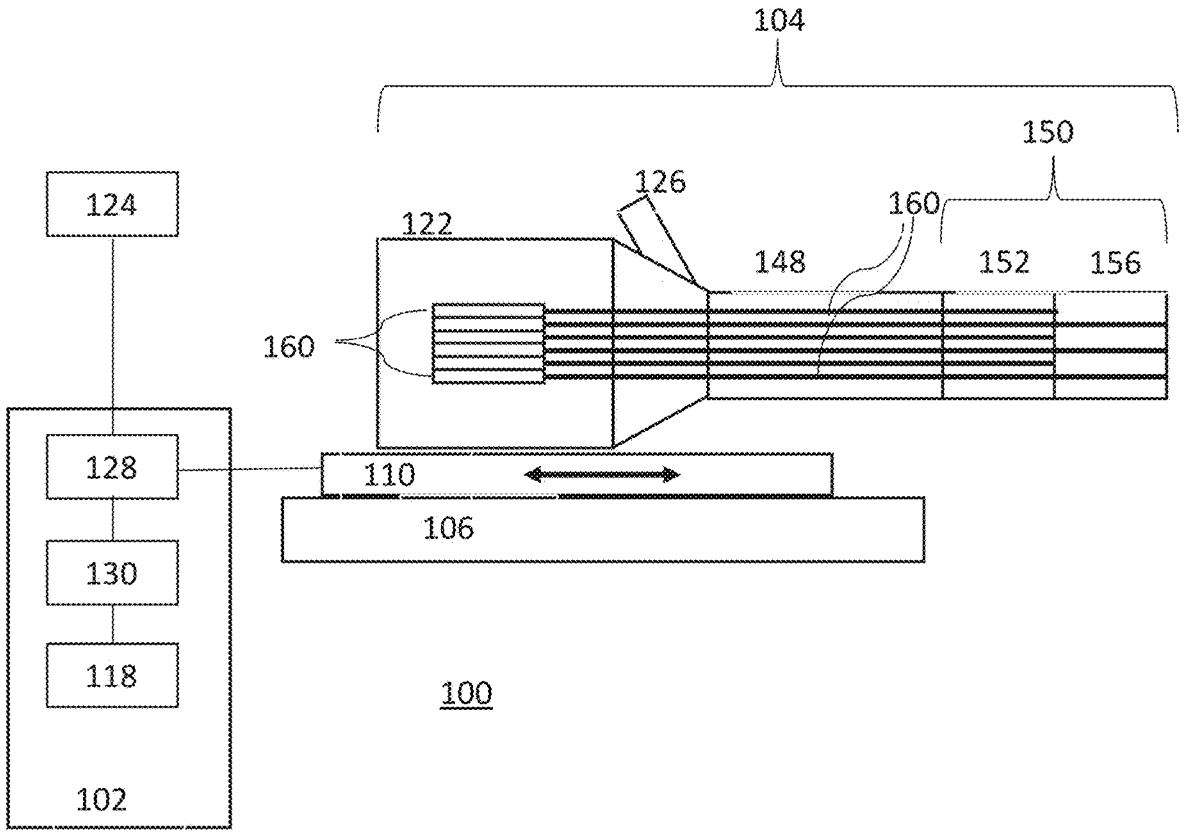
FIG. 2 is a schematic diagram showing at least one embodiment of an imaging, bendable body, or continuum robot apparatus or system in accordance with one or more aspects of the present disclosure.
Figure 3:
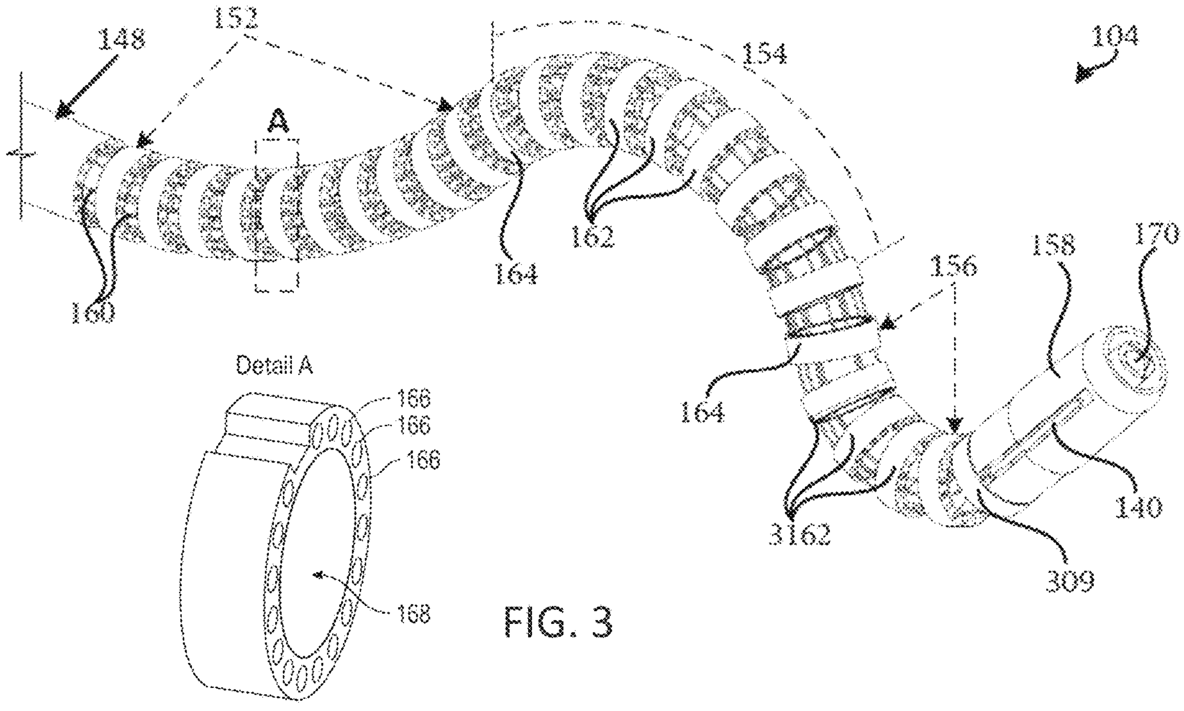
FIG. 3 illustrate at least one embodiment example of a continuum robot and/or medical device that may be used with one or more technique(s), including autonomous navigation technique(s), in accordance with one or more aspects of the present disclosure. Detail A illustrates one guide ring of the bendable body.
Figure 4:
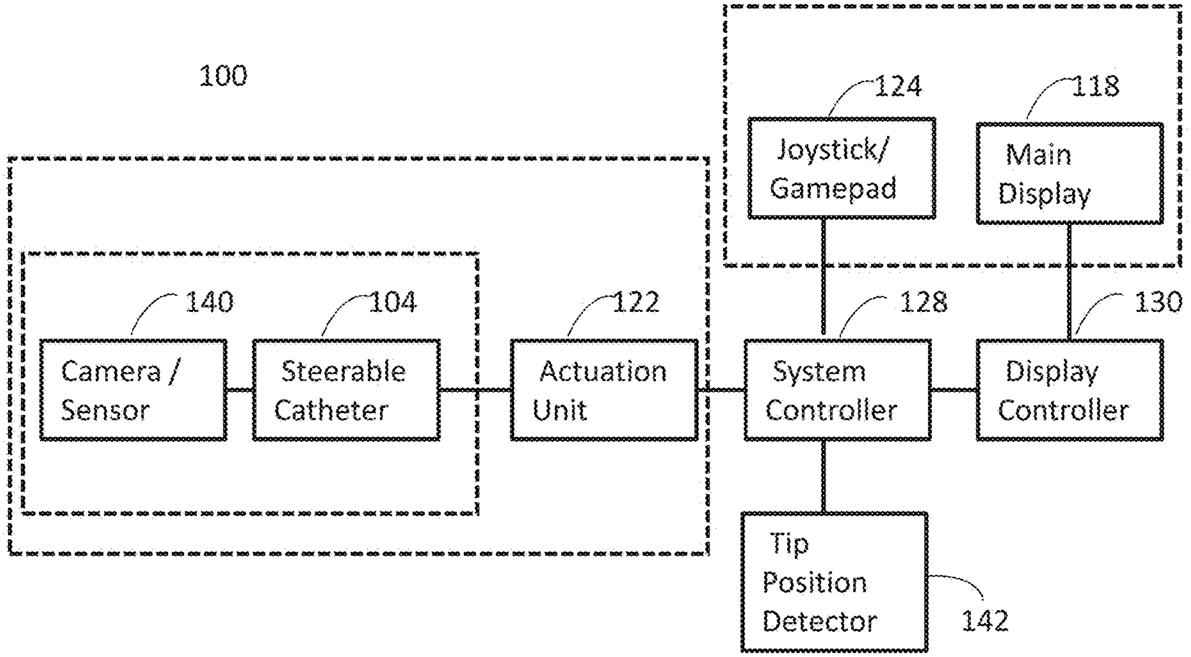
FIG. 4 is a schematic diagram showing at least one embodiment of an imaging, continuum robot, bendable body, or endoscopic apparatus or system in accordance with one or more aspects of the present disclosure.
Figure 5:
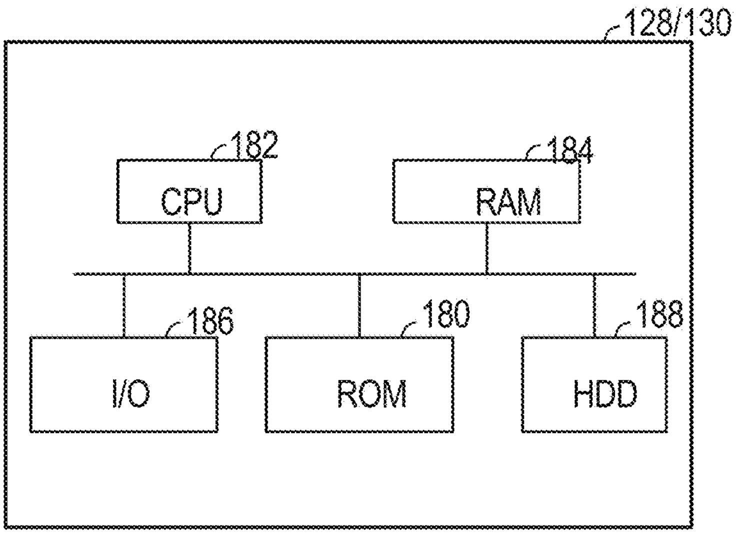
FIG. 5 is a schematic diagram showing at least one embodiment of a console or computer that may be used with one or more autonomous navigation technique(s) in accordance with one or more aspects of the present disclosure.

An embodiment of a robotic catheter system 100 is described in reference to FIG. 1 through FIG. 4. FIG. 1 illustrates a simplified representation of a medical environment, such as an operating room, where a robotic catheter system 100 can be used. FIG. 2 illustrates a functional block diagram of the robotic catheter system 100. FIGS. 3A-C represents the catheter and bending. FIGS. 4-5 illustrates a logical block diagram of the robotic catheter system 100. In this example, the system 100 includes a system console 102 (computer cart) operatively connected to a bendable body 104 via a robotic platform 106. The robotic platform 106 includes one or more than one robotic arm 108 and a linear translation stage 110.

In FIG. 1, A user 112 (e.g., a physician) controls the robotic catheter system 100 via a user interface unit (operation unit) to perform an intraluminal procedure on a patient 114 positioned on an operating table 116. The user interface may include at least one of a main display 118 (a first user interface unit), a secondary display 120 (a second user interface unit), and a handheld controller 124 (a third user interface unit). The main display 118 may include, for example, a large display screen attached to the system console 102 or mounted on a wall of the operating room and may be, for example, designed as part of the robotic catheter system 100 or be part of the operating room equipment. Optionally, there is a secondary display 120 that is a compact (portable) display device configured to be removably attached to the robotic platform 106. Examples of the secondary display 120 include a portable tablet computer or a mobile communication device (a cellphone).

The bendable body 104 may be steerable and is actuated via an actuator unit 122. The actuator unit 103 is removably attached to the linear translation stage 110 of the robotic platform 106. The handheld controller 124 may include a gamepad-like controller with a joystick having shift levers and/or push buttons. It may be a one-handed controller or a two-handed controller. In one embodiment, the actuator unit 122 is enclosed in a housing having a shape of a catheter handle. One or more access ports 126 are provided in or around the catheter handle. The access port 126 is used for inserting and/or withdrawing end effector tools and/or fluids when performing an interventional procedure of the patient 114.

In some embodiments, the handheld controller 124 and/or an integrated controller and/or the GUI have inputs to modify the mode or settings. For example, a change between "Tip Bending" and "Proximal Bending" can be toggled with the push of a button (or similar digital/on-off method). In one scenario, the mode will cycle between the two (or more) modes each time the 'button' is pressed & released. If there are mode than two modes, a method to reverse the direction of the cycling can also be included.

In another scenario, the mode can be toggled based on the state of a digital/on-off input. This input can be something that maintains its state after being changed (like a switch or checkbox) or something that will revert back to the initial state once it is release (i.e. a push button). For example, the mode can be in "Tip Bending" when this state is OFF, and it will switch to "Proximal Bending" when the state is ON. If there are more than two modes, a 'multi-state' input could be implemented, or the mode can be determined based on the combined states of multiple inputs.

The amount of bending applied to each section when in distributed mode can also be adjusted with physical or virtual inputs. In one scenario, the ability to include a section in the distribution can be toggled on/off using manner described in the above paragraph.

In another scenario, the amount of distribution applied to each section can be adjusted. This can be provided with a range input element such as a slider or knob (real or virtual). For example, there can a virtual slider or number box which represents the percentage of the total distribution that is applied to the section. Alternatively, the value of this input can represent the reduction of distribution. For example, a value representing 25% will in turn result in distributing 75% of the input bending amount to the corresponding section. Similarly, these values can be adjusted using physical inputs. These inputs can be analog where the value within its range corresponds to the percentage (or reduction) of distribution of the corresponding section. This input can maintain its state when changed (i.e. a dial) or it can return to its starting state when released (i.e. a trigger). The range input element that is a physical device can also 'adjust' the distribution ratio, rather than directly represent it. For example, a press of a button or a push of an analog stick can increase or decrease the distribution value for the corresponding section. The rate at which it changes can be either fixed, modifiable, or be related to the value of the input (if it is analog).

If there are multiple sections, each section can have its own dedicated input. Alternatively, one input can correspond to multiple sections. In this scenario, they could both be affected in the same manner (i.e., both reduced or increased) or inversely, where one is increased and the other is decreased (or a combination of each if more than 2). This input can be a direct mapping, or an increment/decrement. If the input is an increment/decrement, the rate of increase/decrease could be the same for each, or could be different for each. The adjustment of the rate of each can be modified in similar manners as described in earlier paragraphs.

The system console 102 includes a system controller 128, a display controller 130, and the main display 118. The main display 118 may include a conventional display device such as a liquid crystal display (LCD), an OLED display, a QLED display or the like. The main display 118 provides a graphic interface unit (GUI) configured to display one or more views. These views include live view image 132, an intraoperative image 134, and a preoperative image 136, and other procedural information 138. Other views that may be displayed include a model view, a navigational information view, and/or a composite view. The live image view 132 may be an image from a camera at the tip of the catheter. This view may also include, for example, information about the perception and navigation of the catheter 104. The preoperative image 136 may include pre-acquired 3D or 2D medical images of the patient acquired by conventional imaging modalities such as computer tomography (CT), magnetic resonance imaging (MRI), or ultrasound imaging. The intraoperative image 134 may include images used for image guided procedure such images may be acquired by fluoroscopy or CT imaging modalities. Intraoperative image 134 may be augmented, combined, or correlated with information obtained from a sensor, camera image, or catheter data.

In the various embodiments where a catheter tip tracking sensor 140 is used, the sensor may be located at the distal end of the catheter. The catheter tip tracking sensor 140 may be, for example, an electromagnetic (EM) sensor. If an EM sensor is used, a catheter tip position detector 142 is included in the robotic catheter system 100; this catheter tip position detector would include an EM field generator operatively connected to the system controller 128. Suitable electromagnetic sensors for use with a bendable body are well-known and described, for example, in U.S. Pat. No. 6,201,387 and international publication WO2020194212A1.

Similar to FIG. 1, the diagram of FIG. 2 illustrates the robotic catheter system 100 includes the system controller 128 operatively connected to the display controller 130, which is connected to the display unit 118, and to the hand held control 124. The system controller 128 is also connected to the actuator unit 122 via the robotic platform 106, which includes the linear translation stage 110. The actuator unit 122 includes a plurality of motors 144 that control the plurality of drive wires 160. These drive wires travel through the bendable body 104. One or more access ports 126 may be located on the catheter. The catheter includes a proximal section 148 located between the actuator and the proximal bending section 152 where they actuate the proximal bending section. Three of the six drive wires 160 continue through the distal bending section 156 where they actuate this section and allow for a range of movement. This figure is shown with two bendable sections (152 and 156). Other embodiments as described herein can have three bendable sections (see FIG. 3). In some embodiments, a single bending section may be provided, or alternatively, four or more bendable sections may be present in the catheter.

FIG. 3 shows an exemplary embodiment of a bendable body 104. The bendable body 104 includes a non-steerable proximal section 148, a steerable distal section 150, and a catheter tip 158. The proximal section 148 and distal bendable section 150 (including separate sections 152, 154 and 156) are joined to each other by a plurality of drive wires 160 arranged along the wall of the catheter. The proximal section 148 is configured with thru-holes or grooves or conduits to pass drive wires 160 from the distal section 150 to the actuator unit 122. The distal section 150 is comprised of a plurality of bending segments including a distal segment 156, a middle segment 154, and a proximal segment 152. Each bending segment is bent by actuation of at least some of the plurality of drive wires 160 (driving members). The posture of the catheter may be supported by non-illustrated supporting wires (support members) also arranged along the wall of the catheter (see U.S. Pat. Pub. US2021/0308423). The proximal ends of drive wires 160 are connected to individual actuators or motors 144 of the actuator unit 122, while the distal ends of the drive wires 160 are selectively anchored to anchor members in the different bending segments of the distal bendable section 150.

Each bending segment is formed by a plurality of ring-shaped components (rings) with thru-holes, grooves, or conduits along the wall of the rings. The ring-shaped components are defined as wire-guiding members 162 or anchor members 164 depending on their function within the catheter. Anchor members 164 are ring-shaped components onto which the distal end of one or more drive wires 160 are attached. Wire-guiding members 162 are ring-shaped components through which some drive wires 160 slide through (without being attached thereto).

Detail "A" in FIG. 3 illustrates an exemplary embodiment of a ring-shaped component (a wire-guiding member 162 or an anchor member 164). Each ring-shaped component includes a central opening which forms the tool channel 168, and plural conduits 166 (grooves, sub-channels, or thru-holes) arranged lengthwise equidistant from the central opening along the annular wall of each ring-shaped component. Inside the ring-shaped component, an inner cover such as is described in U.S. Pat. Pub US2021/0369085 and US2022/0126060, may be included to provide a smooth inner channel and provide protection. The non-steerable proximal section 148 is a flexible tubular shaft and can be made of extruded polymer material. The tubular shaft of the proximal section 148 also has a central opening or tool channel 168 and plural conduits 166 along the wall of the shaft surrounding the tool channel 168. An outer sheath may cover the tubular shaft and the steerable section 150. In this manner, at least one tool channel 168 formed inside the bendable body 104 provides passage for an imaging device and/or end effector tools from the insertion port 126 to the distal end of the bendable body 104.

The actuator unit 122 includes one or more servo motors or piezoelectric actuators. The actuator unit 122 bends one or more of the bending segments of the catheter by applying a pushing and/or pulling force to the drive wires 160. As shown in FIG. 3A, each of the three bendable segments of the bendable body 104 has a plurality of drive wires 160. If each bendable segment is actuated by three drive wires 160, the bendable body 104 has nine driving wires arranged along the wall of the catheter. Each bendable segment of the catheter is bent by the actuator unit 122 by pushing or pulling at least one of these nine drive wires 160. Force is applied to each individual drive wire in order to manipulate/steer the catheter to a desired pose. Thus, any segment may be moved by moving at least one of the three drive wires anchored at that segment, and moving at least one drive wire of a segment means that one or more of the drive wires is moved. This can comprise pulling (or pushing) only one of the drive wires, or pulling one while simultaneously pushing on the other(s), etc.

The actuator unit 122 assembled with bendable body 104 is mounted on the linear translation stage 110. Linear translation stage 110 includes a slider and a linear motor. In other words, the linear translation stage 110 is motorized, and can be controlled by the system controller 128 to insert and remove the bendable body 104 to/from the patient's bodily lumen.

An imaging device 170 that can be inserted through the tool channel 168 includes an endoscope camera (videoscope) along with illumination optics (e.g., optical fibers or LEDs). The illumination optics provides light to irradiate the lumen and/or a lesion target which is a region of interest within the patient. End effector tools refer endoscopic surgical tools including clamps, graspers, scissors, staplers, ablation or biopsy needles, and other similar tools, which serve to manipulate body parts (organs or tumorous tissue) during examination or surgery. The imaging device 170 may be what is commonly known as a chip-on-tip camera and may be color or black-and-white.

In some embodiments, a tracking sensor 140 (e.g., an EM tracking sensor) is attached to the catheter tip 158. In this embodiment, bendable body 104 and the tracking sensor 140 can be tracked by the tip position detector 142. Specifically, the tip position detector 142 detects a position of the tracking sensor 140, and outputs the detected positional information to the system controller 100. The system controller 128, receives the positional information from the tip position detector 142, and continuously records and displays the position of the bendable body 104 with respect to the patient's coordinate system. The system controller 128 controls the actuator unit 122 and the linear translation stage 110 in accordance with the manipulation commands input by the user 112 via one or more of the user interface units (the handheld controller 124, a GUI at the main display 118 or touchscreen buttons at the secondary display 120).

The robotic medical system as described herein can include a continuum or multi-segment robot configured to form a curved geometry in one or more planes by actuating one or more bending sections of the bendable body 3. An example of a continuum robot is a snake-like catheter and/or endoscopic device, as described in applicant's previously published U.S. Pat. Nos. 9,144,370; 11,051,892; 11,103,992; 11,278,366; 11,007,641 and patent application publications US2019/0105468; US2021/0386972; US2021/0308423; and US 2022/0126060, which are incorporated by reference herein for all purposes.

FIG. 4 illustrates the system controller 128 executes software programs and controls the display controller 130 to display a navigation screen (e.g., a live view image 132) on the main display 118 and/or the secondary display 120. The display controller 130 may include a graphics processing unit (GPU) or a video display controller (VDC).

FIG. 5 illustrates components of the system controller 128 and/or the display controller 130. The system controller 128 and the display controller 130 can be configured separately. Alternatively, the system controller 128 and the display controller 102 can be configured as one device. In either case, the system controller 128 and the display controller 130 comprise substantially the same components. Specifically, the system controller 128 and display controller 130 may include a central processing unit (CPU 182) comprised of one or more processors (microprocessors), a random access memory (RAM 184) module, an input/output (I/O 186) interface, a read only memory (ROM 180), and data storage memory (e.g., a hard disk drive (HDD 188) or solid state drive (SSD)).

The ROM 180 and/or HDD 188 store the operating system (OS) software, and software programs necessary for executing the functions of the robotic catheter system 100 as a whole. The RAM 184 is used as a workspace memory. The CPU 182 executes the software programs developed in the RAM 184. The I/O 186 inputs, for example, positional information to the display controller 130, and outputs information for displaying the navigation screen to the one or more displays (main display 118 and/or secondary display 120). In the embodiments descried below, the navigation screen is a graphical user interface (GUI) generated by a software program but, it may also be generated by firmware, or a combination of software and firmware.

The system controller 128 may control the bendable body 104 based on any known kinematic algorithms applicable to continuum or snake-like catheter robots. For example, the system controller controls the bendable body 104 based on an algorithm known as follow the leader (FTL) algorithm. By applying the FTL algorithm, the most distal segment 156 of the steerable section 150 is actively controlled with forward kinematic values, while the middle segment 154 and the proximal segment 152 (following sections) of the bendable body 104 move at a first position in the same way as the distal section moved at the first position or a second position near the first position.

The display controller 130 acquires position information of the bendable body 104 from system controller 102. Alternatively, the display controller 130 may acquire the position information directly from the tip position detector 142. The bendable body 104 may be a single-use or limited-use catheter device. In other words, the bendable body 104 can be attachable to, and detachable from, the actuator unit 122 to be disposable.

During a procedure, the display controller 130 can generate and outputs a live-view image or other view(s) or a navigation screen to the main display 118 and/or the secondary display 120. This view can optionally be registered with a 3D model of a patient's anatomy (a branching structure) and the position information of at least a portion of the catheter (e.g., position of the catheter tip 158) by executing pre-programmed software routines. Upon completing navigation to a desired target, one or more end effector tools can be inserted through the access port 126 at the proximal end of the catheter, and such tools can be guided through the tool channel 168 of the catheter body to perform an intraluminal procedure from the distal end of the catheter.

The tool may be a medical tool such as an endoscope camera, forceps, a needle or other biopsy or ablation tools. In one embodiment, the tool may be described as an operation tool or working tool. The working tool is inserted or removed through the working tool access port 126. In the embodiments below, an embodiment of using a bendable body to guide a tool to a target is explained. The tool may include an endoscope camera or an end effector tool, which can be guided through a bendable body under the same principles. In a procedure there is usually a planning procedure, a registration procedure, a targeting procedure, and an operation procedure.

For a medical procedure where the bendable medical device 104 will be used, medical images (e.g., from the CT scanner) are often pre-operatively provided to the robotic catheter system 100. With the robotic catheter system 100, a clinical user creates an anatomical computer model from the images, such as of the lung airways of patient 114. From chest images received from the CT scanner or PACS system, the clinical user can segment the lung airways for clinical treatments, such as a biopsy. After the robotic catheter system 100 generates a map of the lung airways, the user can also use the navigation software system to create a plan to access a lesion for the biopsy. The plan includes the target lesion and a trajectory (navigation path) through the airways to insert the distal section 150 of the bendable body 104.

According to one embodiment, either during insertion or retraction of the bendable body 104, the system controller 128 may control the linear translation stage 110 of the robotic platform 106 to move the bendable body 104 along the center line of a lumen (e.g., an airway) in a desired trajectory followed by active control of the bending segments. This is similar to known shaft guidance techniques used to control robotic guided catheters or endoscopes with the goal of forcing the flexible shaft of the sheath to keep to a desired trajectory. In one example, when using the robotic catheter system 100, the bendable body 104 is robotically controlled to advance through a lumen. The control may be through sensors, the external images, and/or images from the tip of the bendable body. Sensors may be included to measure the actuation force, insertion depth, the angulations of user-controlled steerable segments, etc., to obtain trajectory and other information. After a short advance in insertion or retraction distance, the shape of the bendable body 104 is corrected by adjusting (actuating) one or more of the bending segments in such a way that the new shape closely matches the desired trajectory. This process is repeated until a target area is reached. The same process can be applied when the bendable body is controlled to withdraw the bendable body 104 from the patient. This process is similar to the navigation process described in, e.g., US 2007/0135803, which is incorporated by reference herein for all purposes.

Additional details for driving a bendable body robot include the control methods for actuation, as described in applicant's previous patent application publications US 2015/0088161, US 2018/0243900, US 2018/0311006, and US 2019/0015978, which are also incorporated by reference herein for all purposes.

<Bending Modes>

The bendable body 104 can be actuated to bend each segment independently. While one mode of operation provides for the full control of each bendable segment independently, other modes can be provided that pre-define how the bendable medical device responds to movement commands. For example, in one bending mode, only bending the middle of the three segments provides a "chickenhead" motion. Another bending mode provides for all three bendable segments to bend uniformly.

To provide the multiple bending modes, a control algorithm can apply a different function for each of the bending sections to determine the amount and direction of motion that gets applied. This function will be based on the user (or system) supplied input motion, and can also consider any other number of arguments. Some of these optional arguments include the current control mode, the current/historical pose of each section of the catheter, and the location of the catheter within the anatomy.

Figure 6A:
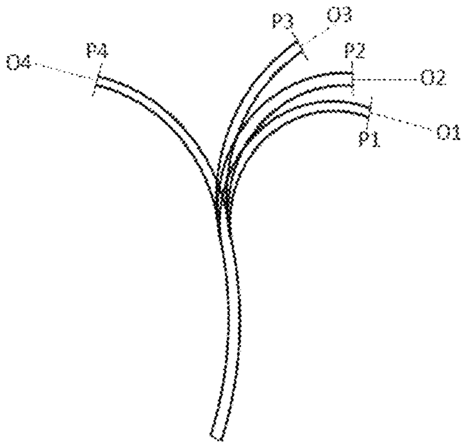
FIGS. 6(A)-6(C) illustrate one or more principles of catheter or continuum robot tip manipulation by actuating one or more bending segments of a continuum robot or bendable body 104 of FIGS. 6(A)-6(C) in accordance with one or more aspects of the present disclosure.
Figure 6B:
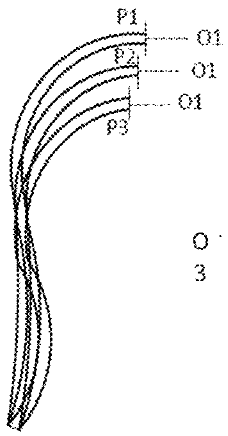
Figure 6C:
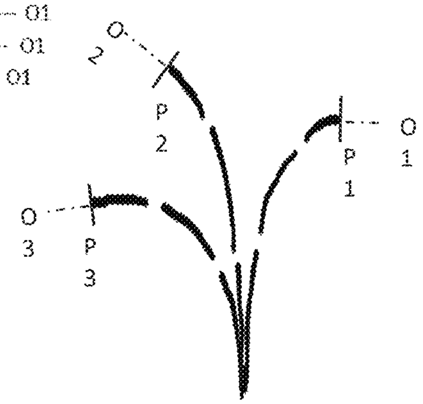

FIGS. 6(A)-6(C) show exemplary catheter tip manipulations by actuating one or more bending segments of the bendable body 104 in different bending modes. As illustrated in FIG. 6(A), manipulating only the most distal segment 156 of the steerable section (tip bending mode) changes the position and orientation of the catheter tip 158. On the other hand, manipulating one or more bending segments (152 or 154) other than the most distal segment affects only the position of catheter tip 158, but does not affect the orientation of the catheter tip. In FIG. 6(A), actuation of distal segment 155 changes the catheter tip from a position P1 having orientation O1, to a position P2 having orientation O2, to position P3 having orientation O3, to position P4 having orientation O4, etc. In FIG. 6(B) actuation of the middle segment 154 changes the position of catheter tip 158 from a position P1 having orientation O1 to a position P2 and position P3 having the same orientation O1. This mode is also described as a Chicken Head mode due to the way the tip can move around the target site like a chicken searching for grain.

Here, it should be appreciated by those skilled in the art that exemplary catheter tip manipulations shown in FIGS. 6(A) and 6(B) can be performed during catheter navigation (i.e., while inserting the catheter through tortuous anatomies). In the present disclosure, the exemplary catheter tip manipulations shown in FIGS. 6(A) and 6(B) apply namely to the targeting mode. In some examples, this mode is applied after the catheter tip has been navigated to a predetermined distance (a targeting distance) from the target. In FIG. 6(C) the bending is distributed through the different bending sections. The actuation of all three segments changes the catheter tip from a position P1 having orientation O1, to a position P2 having orientation O2, to position P3 having orientation O3, etc. While this mode may not be useful in navigating all tightly turning anatomy, as can be seen by comparing FIG. 6(A) with FIG. 6(C), it can be particularly important for tool ingress where the tool may be too long to bend as tightly as was used to navigate to the target site.

For each of these, modes, input data is used to move the catheter segments. Input data may come from a user, an automated system (see, for example, U.S. Provisional applications 63/513,803 and 63/513,794), or a combination thereof. For example, input data includes a selection of operation mode, a target bend from a user via a hand controller or GUI. The target bend can be the bend angle, the bend direction, or a combination. It includes both magnitude and direction. In some embodiments, the function applied to the magnitude and the function applied to the direction can be the same or it can be different.

Alternatively or additionally the input date may be a data representation of target bend, which is a wire position or other kinematic representation that is an alternative expression of the bend angle and/or direction. This data representation may be a translation of the user-defined target bend translated into information the controller uses to control the drive wires.

The target bend may be the bend angle (or direction) for the final target (e.g., bending to the region of interest). In other embodiments, the target bend is a change in bend angle (or direction).

Other input instruction may include the current or prior bend angle of each segment and/or data representation of the current or prior bend angle. This information can be obtained, for example, from a table that stores pose information for a procedure.

Tip Bending mode. In this mode, the controller is configured to move the at least one distal drive towards the target bend, or the data representation of target bend, based on input data. This bend is to the bend angle and/or direction resulting from the prior bend angle and/or prior direction.

Targeting mode. In this mode, the controller is configured to move the at least one proximal drive wire towards the target bend or the data representation based on input data. The proximal drive wire is moved in the case of the bendable body having two bending segments. However, when the bendable body has three or more bending segments, the controller is configured to move only an at least one drive wire to bend the bending segment proximal to the distal bending segment towards the target bend or the data representation of target bend based on input data.

Distributed bending mode. In this mode, the controller is configured to move the at least one proximal drive wire and the at least one distal drive wire simultaneously. This may accomplish bending the proximal bending segment at an angle less than the bend angle and to bend the distal bending segment to the bend angle. These can be in any ratios, the proximal doesn't necessarily have to be less than distal, and neither technically have to utilize the "full" bend angle/direction <Distributed Bending and the Distribution Function>

Figure 7:
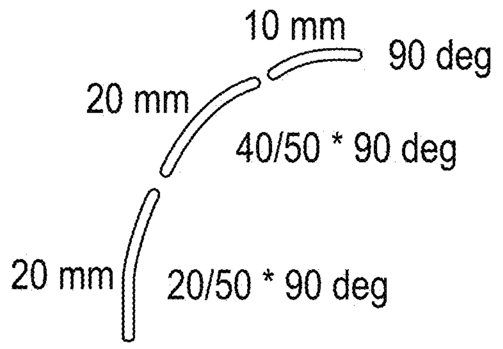
FIG. 7 illustrates Uniform Curvature based on Section Lengths.

The most basic function for distributed bending is a simple proportional amount of the input value. For example to create a uniform curvature using all bending sections, the amount of motion applied to each section will match the percentage of the position the end effector is along the entirety of the combined bending length. This can be seen in FIG. 7. Looking at the exemplary end of the bendable body having three bending segments, the proximal bending segment 152 is seen with a length of 20 mm. The middle segment 154 and distal segment 156 are shown as having a total length of 30 mm for a total bendable length of 50 mm. Thus, for a 90 degree turn of the bendable body in FIG. 7, the proximal bending segment 152 has an angle of 20 mm/50 mm*90 deg.=36 deg., which is the percentage of the position of the end effector along the combined bending length. The middle bending segment 154 will have an amount of motion applied to match the equation 40 mm/50 mm*90 deg.=72 deg. since this segment is 40 mm from the base position and the total length is 50 mm. The distal segment 156 will have the full 90 deg. bend.

While FIG. 1 is shown for a three section bendable body having the lengths of 20, 20, and 10 mm, other embodiments can have two, four, or more sections that have the same or different lengths. The important consideration for this most basic function of distributed bending is that the proportional amount of the input value remains constant. For example, a four section robot with each section having a 20 mm length, with a target bend of 60 degrees, would have a distal segment bending at 15 deg., the middle segments bending at 30 and 45 deg., and the proximal segment bending at the listed 60 deg.

Similarly, Tip Bending and Chickenhead motion (as shown in FIGS. 6(A) and 6(B)) fall under this algorithm if this control mode is included in the function. In Tip Bending mode, the tip receives 100% of the motion while all other sections receive 0% (FIG. 6(A)). Likewise, in Targeting/Chickenhead mode (FIG. 6(B)), the middle segment receives 100% of the motion while all other sections received 0%.

However, there are certain functions that are not possible with targeting and chicken head motion. For example, there are certain tools that are very stiff at the distal portion. This can restrict the amount of local bending that the tip can achieve. (Local bending is the relative pose between the tip and middle segments). In this scenario, if the user wanted to bend the catheter in a direction that the tool is prohibiting, the motion can be applied to both the tip and middle segment equally in a distributed bending mode (FIG. 10(B). This will therefore change the tip orientation without changing the local pose.

This simple ratio distribution can also be used to implement functions that are not currently possible with other systems.

The table below is a simple example of the aforementioned examples with a catheter having three bendable sections of 10, 20, and 20 mm.

TABLE 1

Movement Modes for 10 mm/20 mm/20 mm Catheter

| | Distal % | Middle % | Proximal % |
|---|---|---|---|
| Tip Bending Mode | 100 | 0 | 0 |
| Chickenhead Mode | 0 | 100 | 0 |
| Orientation Mode (Change Tip Orientation without Changing Local Pose) | 100 | 100 | 0 |
| Distributed Bending Mode | 100 | 80 | 40 |

Figure 11:
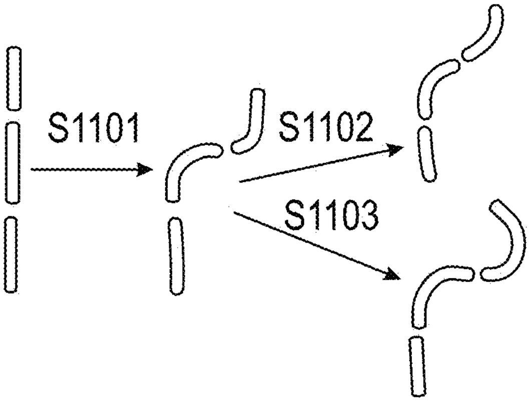
FIG. 11 illustrates counteractions that can be taken in a pose having a bendable middle segment to remove effects of cross-talk to maintain output orientation.

This distribution function does not merely have to modify the amount of motion; it can also affect the direction. This will be useful for Chickenhead motion. The desired effect of chickenhead motion is to translate the tip position without changing the orientation. It achieves this by bending the middle segment. However, due to the physics of the catheter design, the orientation of the tip will change slightly as the middle segment moves. As shown in FIG. 11, this sort of motion can be counteracted by applying a bending to the tip to offset the resultant motion from the middle segment bending. The direction of this would typically be in the opposite direction of the middle segment motion.

The amount of bending to be applied, however, would depend on the local pose of the tip. A consequence of bending the middle segment is that the local pose of the tip section will change. As mentioned earlier, the local pose is the relative pose between the tip section and the middle segment. One physical phenomenon of the three-section catheter is that output ratio is inversely proportional to its local pose. In other words, the same drive wire positions will produce a lower output angle as the local pose angle increases. Therefore, the degree to which the tip orientation will change from chickenhead motion will vary based on how its local pose changes. So the function to counteract this unintended tip orientation change will have to use the local pose in its calculations.

Finally, if the same basic ratio distribution is applied to the catheter motion from the start of control, then the resultant pose of all sections at any point during the operation is in the same ratio distribution.

Figure 8:
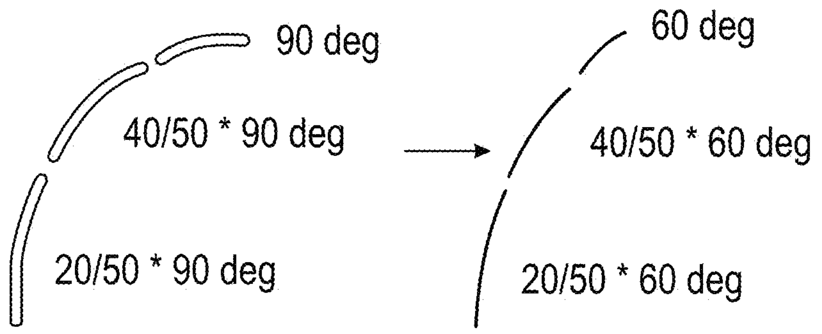
FIG. 8 illustrates a pose having a uniform curvature distribution at 90 degrees that is moved by a uniform curvature distribution at 30 degrees.
Figure 9:
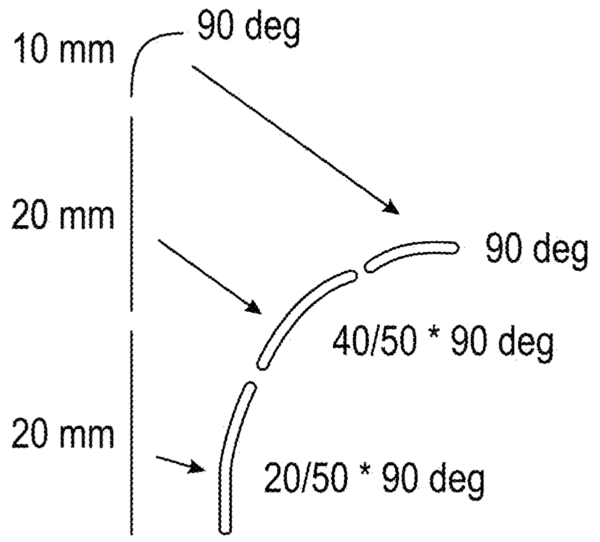
FIG. 9 illustrates the transitioning into a uniform curvature distribution.

In FIG. 8, a catheter with the uniform curvature distribution (at 90 degrees) gets applied a uniform curvature distribution motion of 30 degrees. The resultant pose is still a uniform curvature distribution (at 60 degrees).

However, the pose of the catheter before applying any sort of distributed bending motion is not required to be distributed in the same ratio at the motion. In other words, any sort of distributed bending motion algorithm can be applied to any sort of catheter pose (See FIG. 12). They are independent of each other.

One significant implementation of this is during simple navigation. There are scenarios where the catheter tip bending alone is not sufficient to orient the tip in the desired direction because it reaches its physical limits (the local pose is too high). In prior catheters, when this happens, the stage is driven forward and the FTL algorithm moves the middle segment towards the tip direction. This will reduce the local pose of the tip section, permitting it the ability to continue aiming in the direction it was not able to reach previously. (i.e., increase the local pose further).

This utility, of slightly moving the middle segment in the direction that the tip is trying to aim, can be replicated using this distributed bending. By applying a partial motion to the middle segment, and optionally the proximal segment, to shift the entire bending portion in the direction that the tip is bending, the utility is achieved. This will reduce the amount of local pose increase that occurs during bending, permitting the tip to bend further than it otherwise would be able to bend. Again, the amount of bending that gets applied to the middle/proximal segment could be a function of the local pose. The larger the local pose, the more benefit is obtained from directing the middle segment to move by a larger amount. This could also improve FTL efficiency, as the local pose will be less than it would be without distributed bending mode.

Finally, the functions can also be entirely user define, or have certain parameters that are user defined, and can be adjusted at any point (manually or automatically). One scenario where it would be beneficial to have them change "automatically" could be implemented for "cascading bending".

In another type of distributed bending mode, the bendable device is initially bent with uniform curvature as discussed above. However, when a specified limit has been reached, the controller stops the motion of the proximal most section but continues the motion in the more distal segments. If there are more than 2 bending sections, this cycle can repeat of all sections.

In yet another example, where the Tip Bending mode is initially used, this mode is used until a local pose limit has been reached. When this occurs, any further bending will then also be applied to both the distal segment and the prior segment (the middle segment in a 3-section catheter). If the catheter has more than 2 sections, this sequence can repeat.

The bending does not have to be limited to a single section at a time, it can be distributed through a manner explained in the previous section, but still follow the same paradigm of applying the motion in the other sections once a limit has been reached.

In some embodiments, the constant curvature mode as described in WO/2023/164047 to Takagi may be used. This publication describes a bendable body that is bent by a controller that is configured to switch between first control for bending the first bending portion and second control for bending the first and second bending portions so they have constant curvature. WO/2023/164047 is hereby incorporated by reference in its entirety.

<Transitioning into a Derived Pose>

The user can transition into any distributed pose from any other pose. When this happens, the pose of all sections will be adjusted to match the desired distribution based on the tip's pose. Optionally, the use can only apply this transition to specific sections.

The user can also have the option to revert back to the prior pose from a distributed pose (or, they can select which sections should be reverted, while maintaining others). Finally, the user can change the distributed bending ratio (i.e. enter chickenhead mode) from this distributed pose mode. The would have the option to also change the current pose to match the new distribution, or only have the distribution be applied during bending.

It is also possible for this transition to be applied at a gradual basis, and the user can stop it at any point during the transition if a more desirable pose calls for it.

When transitioning into a distributed pose, the orientation of the tip should remain the same, but the position in space would change. This position change might be able to be accounted for, either manually or automatically, by moving the stage position or bending other sections accordingly.

Also, the function to determine the pose of each section does not have to be based on the tip pose, it can be based on the pose of any section and/or other information such as target location, etc.

<Additional Distribution Functions>

In some embodiments, the distribution functions of bending through more than one bending section.

Figure 10A:
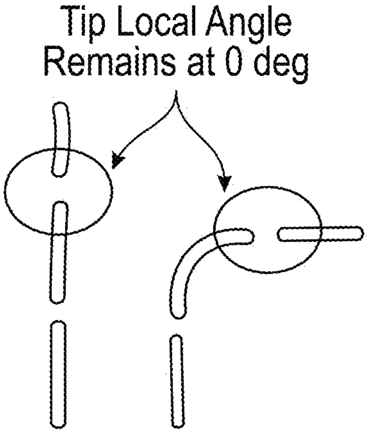
FIGS. 10(A) and 10(B) illustrates maintaining local angle to while still changing orientation.
Figure 10B:
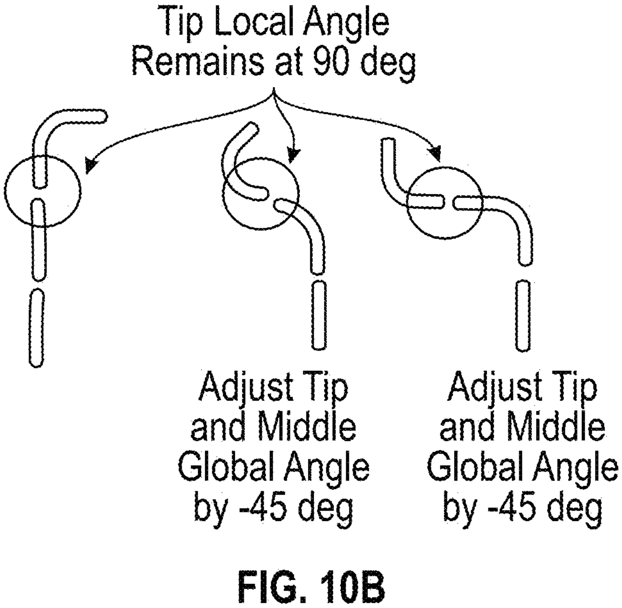

One function provides for improved maintenance of the local pose is the Orientation Mode, shown in FIGS. 10(A) and 10(B). The local angle is maintained while still changing the orientation. For a three-section robot, the configuration is the distal segment is at 100%, the middle segment is at 100%, and the proximal segment is at 0%. As shown in FIG. 10(A), the distal segment is straight, relative to the middle segment. When a bend command of 90 deg. is sent, the result is that the distal and middle segments both aiming towards 90 deg and the distal segment is still straight relative to the middle. In FIG. 10(B), the scenario is that the distal segment is at +90 deg, relative to the middle segment. When a bend command of −45 deg. is sent, the result is that the distal and middle segments both change aiming direction by −45 deg. The distal segment is still bent +90 deg. relative to the middle segment.

Another function of distributed bending relates to Chickenhead mode. In standard Chickenhead mode, the middle segment is bent while the distal and proximal are not. However, there is often some cross-talk between the distal and middle segments and the true final orientation is not accurate. As shown in the example of FIG. 11, all three sections are straight in the three-section robot. A command to bend 90 degrees is sent [S1101] to provide a middle segment bent by 90 deg. However, the true output shape of the standard Chickenhead mode is shown through the bending of where the tip of the distal segment is pulled slightly towards the middle segment bending direction. The tip local angle is reduced and the tip is no longer aiming straight ahead. With a distributed function, shown in step [S1103], the distal segment is bend in the opposite direction of the middle segment bend ([S1101]) to counteract the pull of the middle segment bending on the distal segment. This increases the local angle at the tip and the output direction remains straight ahead.

In yet another example of a distributed function, the middle and/or proximal segment can be "nudged" towards the tip. The settings of an example of this mode are:

TABLE 2

| Movement Mode for 10 mm/20 mm/20 mm Catheter | | | |
|---|---|---|---|
| | Distal % | Middle % | Proximal % |
| Nudge | 100 | 20 | 10 |

Figure 12A:
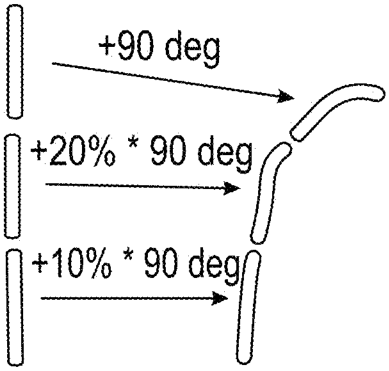
FIGS. 12(A) and 12(B) illustrate a movement mode that allows for smaller movements of the middle and proximal segments, relative to tip movement.
Figure 12B:
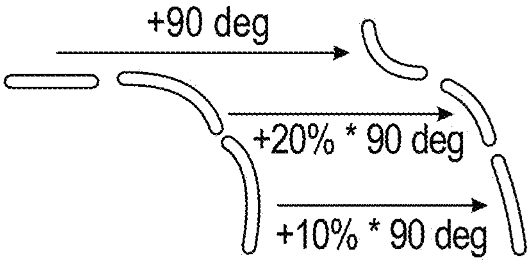

This can be used to reduce the local angle to increase output. As shown in FIG. 12(A), all sections are straight. When a command to bend +90 deg is sent, the distal segment bends 90 deg., the middle segment bends 20%, or 18 deg. and the proximal segment bends 10%, or 9 deg. All the bending occurs in the direction of the tip bending. This can be seen differently in FIG. 12(B) where all sections are angled left, with varying angles at the start of the movement. When a +90 deg. bend command is sent in this case, the distal segment bends by 90 deg., the middle segment bends by 18 deg, and the proximal segment bends by 9 degrees, all in the direction of tip bending. However, the overall shape of this final curve is as if the tip of the robot moves as directed and the other sections are nudged in the direction of the bend to provide a shape that may be particularly useful when navigating and working within a lumen.

In other embodiments, the amount of the nudge may be greater (e.g., 30% and 15%) or less (e.g., 10% and 5%), or may be at a different proportion (e.g., 30% and 10%).

As discussed above, the robotic medical system as described herein can include a continuum or multi-segment robot configured to form a curved geometry in one or more planes by actuating one or more bending sections of the bendable body 3. When two or more of the bending sections are bent, the curvature in these sections may be in two different planes. In some embodiments, the two or more bending sections are bent within the same plane but with different curvatures. For example, when if the tip and proximal sections are bent along perpendicular planes, and the tip bends to increase it's angle along the same plane, the pose of the proximal section will be "nudged" in such a manner that (along with a slight angle change) the bend plane will align closer to the tip's plane. Similarly, the tip section and proximal section can be bending on the same plane, but in different directions. In this case, if the user commands the tip section to bend further, a "nudge" of the proximal section will slightly decrease it's bend amount as it's bend angle was slightly adjusted to move towards the tip.

The present disclosure and/or one or more components of devices, systems, and storage mediums, and/or methods, thereof also may be used in conjunction with continuum robot devices, systems, methods, and/or storage mediums and/or with endoscope devices, systems, methods, and/or storage mediums. Such continuum robot devices, systems, methods, and/or storage mediums are disclosed in at least: U.S. Pat. Nos. 10,687,694; 11,007,641; 11,051,892; 11,096,552; 11278366; 11,504,501; 11,559,190; 11,571,268; and 11,622,828; U.S. Pat. Publications 2020/0375665; 2021/0121051; 2021/0121162; 2021/0259521; 2021/0259790; 2021/0259794; 2021/0260339; 2021/0260767; 2021/0308423; 2021/0362323; 2021/0369085; 2021/0369355; 2021/0369366; 2021/0386972; 2021/229277; 2022/0016394; 2022/0039635; 2022/0039784; 2022/0040450; 2022/0126060; 2022/0202273; 2022/0202277; 2022/0202500; 2022/0202501; 2022/0202502; 2022/0203071; 2023/0016761; 2023/0201522; 2023/0137954; and 2023/0255442 as well as international Publication numbers WO2021/142272; WO2022/031995; WO2022/032162; WO/2023/154352; WO/2023/154825; WO/2023/154931; WO/2023/150162; WO/2023/154713; WO/2023/154246; and WO/2023/154931, the disclosure of each of which are incorporated by reference herein in their entirety. Any of the features of the present disclosure may be used in combination with any of the features as discussed in the patents and applications above.

Definitions

Throughout the figures, where possible, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "includes", "including," and "containing" are to be construed as open-ended terms (i.e., meaning "including, but not limited to,") unless otherwise noted. Specifically, these terms, when used in the present specification, specify the presence of stated features, integers, steps, operations, elements, and/or components, but do not preclude the presence or addition of one or more other features, integers, steps, operations, elements, components, and/or groups thereof not explicitly stated. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

The present disclosure generally relates to medical devices, and it exemplifies embodiments of a bendable body sheath for guiding a catheter and/or an optical probe which may be applicable to an imaging apparatus (e.g., an endoscope). The imaging apparatus may image using a miniature camera based on chip-on-tip (COT) technology, or may provide some other form of imaging such as spectrally encoded endoscopy (SEE) imaging technology (see, e.g., U.S. Pat. Nos. 10,288,868 and 10,261,223). In some embodiments, the imaging apparatus may include an optical coherence tomographic (OCT) apparatus, a spectroscopy apparatus, or a combination of such apparatuses (e.g., a multi-modality imaging probe).

The embodiments of the bendable medical device and portions thereof are described in terms of their position/orientation in a three-dimensional space. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to a total six degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The catheter may be solely an imaging apparatus or it may comprise tools for use in therapeutic or diagnostic procedures. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

It will be appreciated that the methods and compositions of the instant disclosure can be incorporated in the form of a variety of embodiments, only a few of which are disclosed herein. Variations of those embodiments may become apparent to those of ordinary skill in the art upon reading the foregoing description. Skilled artisans are expected and understood to employ such variations as appropriate, and the present disclosure is intended to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

The invention claimed is:

1. A robot system, comprising:

a bendable body having a steerable distal section comprising:

a distal bending segment that is bendable by at least one distal drive wire; and a proximal bending segment that is bendable by at least one proximal drive wire;

one or more first actuators configured to drive the at least one distal drive wire;

one or more second actuators configured to drive the at least one proximal drive wire;

a controller for controlling the first and second actuators based on an input data of:

an operation mode and at least one of: a target bend, or a data representation of target bend;

wherein the operation mode includes at least:

Distributed bending mode, wherein the controller is configured to move the at least one proximal drive wire and the at least one distal drive wire simultaneously, wherein the amount of motion applied to the at least one proximal drive wire matches the percentage of the position the proximal bending segment is along the bendable body, and wherein the amount of motion applied to the at least one distal drive wire matches the percentage of the position the distal bending segment is along the bendable body.

2. The robot system of claim 1, wherein, in the distributed bending mode, the controller is configured to move the at least one proximal drive wire and the at least one distal drive wire such that the distal bending segment and the proximal bending segment are each bent at a pre-determined ratio of bend angle.

3. The robot system of claim 2, wherein, the predetermined ratio for a bending segment is defined as: (length from proximal end of the steerable distal section to a distal end of the bending segment)/(length of the steerable distal section).

4. The robot system of claim 1, wherein, in the distributed bending mode, a local bend angle of the proximal bending segment is less than, but in the same direction, as the input data.

5. The robot system of claim 1, wherein the controller is configured to cause the distal bending segment and the proximal bending segment to transition into a specific bend angle based on the input data, where the input data further includes a prior bend angle.

6. The robot system of claim 1, wherein the controller is configured to cause the distal bending segment and the proximal bending segment to transition into a specific bend angle when the controller receives input data of a new operation mode so that resultant bending angle is maintained between the previous and new operation modes.

7. The robot system of claim 1, wherein the controller is configured to cause the distal bending segment and the proximal bending segment to move back to a prior pose.

8. The robot system of claim 1, wherein the controller is further configured to instruct the bendable body to move distally or proximally a distance that relates to the dislocation at a distal tip due to movement of the first and second actuators.

9. The robot system of claim 1, further comprising a middle bending segment that is bendable by at least one middle drive wire, and wherein, for the distributed bending mode, the controller is configured to simultaneously move the at least one proximal drive wire, the at least one middle drive wire, and the at least one distal drive wire.

10. The robot system of claim 1, further comprising a plurality of additional bending segments that are bendable by a plurality of additional drive wire-wires, and wherein, for the distributed bending mode, the controller is configured to simultaneously move the at least one proximal drive wire, the plurality of additional drive wires, and the at least one distal drive wire.

11. The robot system of claim 1, wherein the operation mode is selectable between the Distributed Bending mode and at least one of:

(a) Tip Bending mode, wherein the controller is configured to move the at least one distal drive wire to bend the distal bending segment towards the target bend, or the data representation of target bend, based on the input data; and (b) Targeting mode, wherein the controller is configured to move the at least one proximal drive wire to bend the proximal bending segment towards the target bend or the data representation of the target bend based on the input data in the case of the bendable body having two bending segments, and wherein the controller is configured to move only a drive wire other than the at least one distal drive wire to bend a bending segment proximal to the distal bending segment towards the target bend or the data representation of target bend based on the input data in the case of the bendable body having three or more bending segments.

12. The robot system of claim 11, wherein the input data for the tip bending mode and the targeting mode is provided from an on-off toggle element and the input data for the distributed bending mode is provided from a range input element.

13. A robot system, comprising:

a bendable body having a steerable distal section comprising:

a distal bending segment that is bendable by at least one distal drive wire; and a proximal bending segment that is bendable by at least one proximal drive wire;

one or more first actuators configured to drive the at least one distal drive wire;

one or more second actuators configured to drive the at least one proximal drive wire;

a controller for controlling the first and second actuators based on an input data of:

an operation mode and at least one of: a target bend, or a data representation of target bend;

wherein the input data of operation mode includes the selection of a Distributed bending mode, wherein the controller is configured to move the at least one proximal drive wire and the at least one distal drive wire simultaneously, wherein the amount of motion applied to the at least one proximal drive wire matches the percentage of the position the proximal bending segment is along the bendable body, and wherein the amount of motion applied to the at least one distal drive wire matches the percentage of the position the distal bending segment is along the bendable body.

14. The robot system of claim 13, wherein, in the distributed bending mode, the controller is configured to move the at least one proximal drive wire and the at least one distal drive wire such that the distal bending segment and the proximal bending segment are each bent at a pre-determined ratio of bend angle.

15. The robot system of claim 13, wherein, in the distributed bending mode, local bend angle of the proximal bending segment is less than, but in the same direction, as the input data.

16. The robot system of claim 13, wherein the controller is configured to cause the distal bending segment and the proximal bending segment to transition into a specific bend angle based on the input data, where the input data further includes a prior bend angle.

17. The robot system of claim 13, wherein the operation mode further includes a tip bending mode and a targeting mode, and where the input data for the tip bending mode and the targeting mode is provided from an on-off toggle element and the input data for the distributed bending mode is provided from a range input element.

* * * * *